(12) United States Patent
Hankh et al.

(10) Patent No.: US 6,818,015 B2
(45) Date of Patent: Nov. 16, 2004

(54) CONICAL STENT

(75) Inventors: Susanne Hankh, Villmergen (CH);
Marc Gianotti, Wiesendangen (CH);
Eugen Hofmann, Zurich (CH)

(73) Assignee: Schneider (Europe) GmbH, Bülach (CH)

( * ) Notice: Subject to any disclaimer, the term of this patent is extended or adjusted under 35 U.S.C. 154(b) by 30 days.

(21) Appl. No.: 10/378,528

(22) Filed: Mar. 3, 2003

(65) Prior Publication Data
US 2003/0139804 A1 Jul. 24, 2003

Related U.S. Application Data

(62) Division of application No. 09/946,403, filed on Sep. 4, 2001, now Pat. No. 6,538,810, which is a division of application No. 09/350,704, filed on Jul. 9, 1999, now Pat. No. 6,283,992, which is a division of application No. 08/581,714, filed on Dec. 29, 1995, now Pat. No. 6,922,019.

(30) Foreign Application Priority Data

Nov. 27, 1995 (EP) .............................................. 95118605

(51) Int. Cl.[7] ................................................. A61F 2/06
(52) U.S. Cl. ........................ 623/1.16; 623/1.3; 623/1.23
(58) Field of Search ............................... 623/1.11–1.16, 623/1.3, 1.23, 1.1, 1.31

(56) References Cited

U.S. PATENT DOCUMENTS

| | | | |
|---|---|---|---|
| 3,818,511 A | 6/1974 | Goldberg et al. .................. 3/1 |
| 4,441,215 A | 4/1984 | Kaster ............................. 3/1.4 |
| 4,655,771 A | 4/1987 | Wallsten ......................... 623/1 |
| 4,733,665 A | 3/1988 | Palmaz ....................... 128/343 |
| 4,743,251 A | 5/1988 | Barra ............................. 623/1 |
| 4,800,882 A | 1/1989 | Gianturco .................. 128/343 |
| 4,820,298 A | 4/1989 | Leveen et al. ................. 623/1 |
| 4,856,516 A | 8/1989 | Hillstead ..................... 128/343 |
| 5,061,275 A | 10/1991 | Wallsten et al. ............... 623/1 |
| 5,064,435 A | 11/1991 | Porter .......................... 623/12 |
| 5,330,500 A | 7/1994 | Song .......................... 606/198 |
| 5,383,925 A | 1/1995 | Schmitt ......................... 623/1 |
| 5,562,725 A | 10/1996 | Schmitt et al. ................. 623/1 |
| 5,575,818 A | 11/1996 | Pinchuk ......................... 623/1 |
| 5,645,559 A | 7/1997 | Hachtman et al. .......... 606/198 |
| 5,667,486 A * | 9/1997 | Mikulich et al. .............. 604/8 |

(List continued on next page.)

FOREIGN PATENT DOCUMENTS

| | | |
|---|---|---|
| DE | 3918736 A1 | 12/1990 |
| DE | 19713214 A1 | 12/1998 |
| EP | 183372 A1 | 6/1986 |
| EP | 621015 A1 | 10/1994 |
| EP | 775471 A1 | 5/1997 |
| EP | 804909 A2 | 11/1997 |
| EP | 895761 A2 | 2/1999 |
| EP | 928604 A1 | 7/1999 |

OTHER PUBLICATIONS

Endoscopy 1992: 24: 416–420 "Silicone–Covered Expandable Metallic Stents in the Esophagus: An Experimental Study".

*Primary Examiner*—Corrine McDermott
*Assistant Examiner*—Hieu Phan
(74) *Attorney, Agent, or Firm*—Larkin Hoffman Daly & Lindgren Ltd.; Frederick W. Niebuhr, Esq.

(57) ABSTRACT

The stent having a flexible self-expandable braided tubular wall having a proximal segment having an outer diameter, and a distal segment having an outer diameter smaller than the outer diameter of the proximal segment. An intermediate segment is formed between the proximal and distal segments, which forms a truncated cone of which the base is forming the proximal end of the intermediate segment and of which the top is forming the distal end of the intermediate segment. A covering layer is arranged within the tubular wall.

34 Claims, 5 Drawing Sheets

U.S. PATENT DOCUMENTS

| | | | |
|---|---|---|---|
| 5,741,325 A | 4/1998 | Chaikof et al. | 623/1 |
| 5,741,333 A | 4/1998 | Frid | 623/12 |
| 5,755,769 A | 5/1998 | Richard et al. | 623/11 |
| 5,888,201 A * | 3/1999 | Stinson et al. | 623/1.2 |
| 5,899,935 A | 5/1999 | Ding | 623/1 |
| 5,922,019 A | 7/1999 | Hankh et al. | 623/1 |
| 5,957,974 A | 9/1999 | Thompson et al. | 623/1 |
| 6,051,021 A | 4/2000 | Frid | 623/1 |
| 6,249,952 B1 | 6/2001 | Ding | 29/460 |
| 6,283,992 B1 * | 9/2001 | Hankh et al. | 623/1.2 |
| 6,488,705 B2 | 12/2002 | Schmitt et al. | 623/1.18 |

* cited by examiner

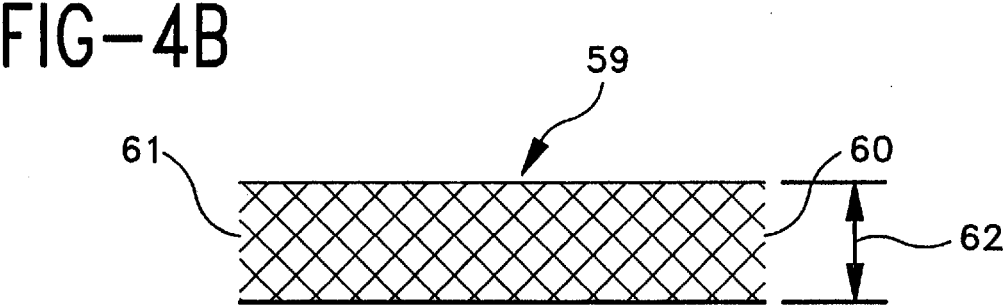
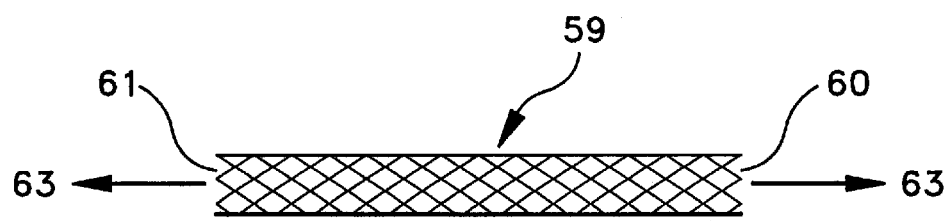
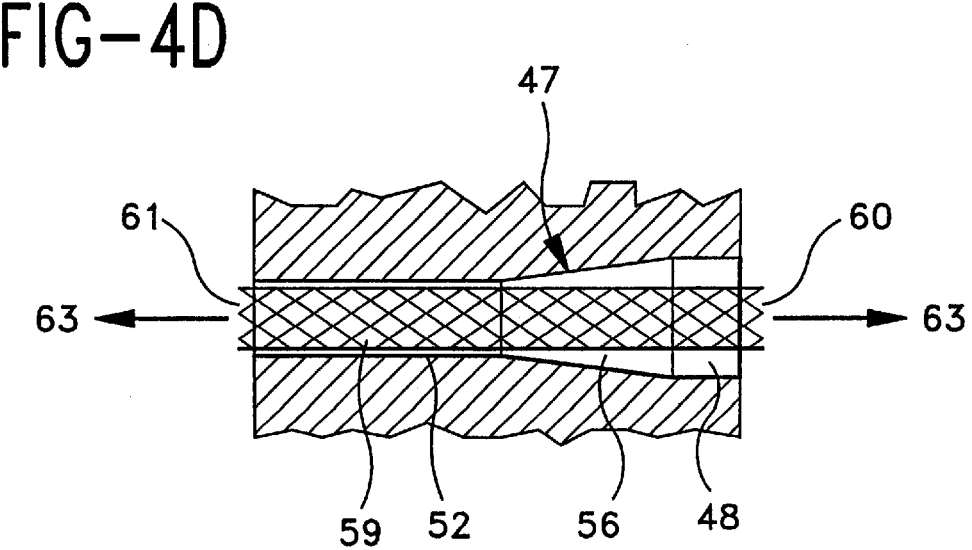

CONICAL STENT

This is a divisional of application Ser. No. 09/946,403 (now U.S. Pat. No. 6,538,810), filed Sep. 4, 2001 as a divisional of application Ser. No. 09/350,704 (now U.S. Pat. No. 6,283,992), filed Jul. 9, 1999 as a divisional of application Ser. No. 08/581,714 (now U.S. Pat. No. 5,922,019), filed Dec. 29, 1995.

BACKGROUND OF THE INVENTION

This invention relates to a stent for use in a body passageway, comprising a flexible self-expandable braided tubular wall. The invention also relates to methods for manufacturing such a stent.

Use of expandable stents is known for damaged areas of body vessels such as for example food pipes, for dilatation, repair or bridging such areas. Where a patient suffers, for example, from a cancer of the esophagus while being otherwise in good status, stenting is a valuable approach to help him living. As such stents are subjected to stresses, in particular due to movements of the duct such as peristaltic movements, there is a tendency for the stent to migrate along the duct where it is placed. When the stent is used for a tumor at the end of a food pipe, for example at the junction of the esophagus and stomach, the problem of migration is further enhanced because the stent may have to protrude into the stomach. In such a case, the problem of anchoring the stent in the duct becomes particularly critical because the stent may fall into the stomach. A further problem arising with stents is that they have a tendency to close the pipe in curved areas thereof because of their deformation.

The document "Endoscopy 1992:24:416–420" describes a covered expandable metallic stent for preventing ingrowth of malignant structures. This stent is made of a steel wire bent in a zig-zag pattern and the stent legs are connected to wire skirts at each end which are intended to improve anchorage of the stent in a body passageway. In addition, 1 mm. barbs are attached to the skirts to still further enhance anchorage of the stent in the passageway. However, the document specifically outlines that migration remains a problem despite the wire skirts and barbs which were provided for anchorage purposes. Such a structure will certainly not allow safe anchoring of the stent in a condition where the stent cannot anchor at one of its ends, as in the case of a tumor at the end of the esophagus. And there are no solutions to overcome the pipe closure due to deformation of the stent in curved areas.

U.S. Pat. No. 4,655,771 discloses a stent made of a flexible tubular braided structure formed of helically wound thread elements. When the stent is deployed the stent assumes a substantially cylindrical shape as it expands and substantially conforms to the vessel wall, and the document outlines that such an expansion allows the stent to stay in place by self-fixation because of the permanent pressure of engagement against the vessel wall. Such a configuration may provide a good fixation in smooth rectilinear areas of the vessel. However, it will not provide a safe fixation in areas where a part of the stent cannot bear against the vessel wall. Nor will it solve the problem of pipe closure in curved areas of the vessel.

U.S. Pat. No. 5,064,435 shows a body implantable stent consisting of two or more generally tubular, coaxial and slidably joined stent elements each of which is of open weave construction, formed of multiple braided, helically wound strands of resilient material. The stent is thus elastically deformed to a reduced radius when deployed and it self expands radially when released after positioning in a vessel or other body cavity. To match the axial contraction of the stent upon radial expansion thereof and preserve a consistent length of the stent in spite of the axial contraction of the overlapping stent elements, the axially outward and non-overlapping portions of the stent are designed as radially outward flares to secure fixation of the stent to the vessel wall. Accordingly, axial contraction of the stent occurs as a reduction in the length of the medial region where the stent elements overlap. Other means to maintain the axial length comprise reinforcing filaments near the opposite ends of the stent elements to increase the restoring force, or fixation of hooks at the opposite ends of the stent elements, or still an elongate axially directed flexible and inextensible wire secured to the opposite ends of the stent elements. Such a configuration cannot be safely used if both the ends of the stent elements are not very strongly affixed to the vessel wall. As a matter of fact, if one of the stent elements is not firmly secured to the vessel wall, it may migrate with respect to the other stent element, for example because of peristaltic movements, whereby there may be a separation of the overlapping stent elements; where the stent is to be used at a place such as the junction of the esophagus to the stomach, the unsecured stent element will fall into the stomach. Complete separation of the stent elements will not occur in the case of use of an inextensible wire secured to opposite ends of the stent elements; however, such a wire cannot prevent part separation of the stent elements, for instance where the stent takes a relatively sharply curved configuration, which may cause serious injury to the vessel wall. And furthermore, whatever its configuration, the overlapping arrangement may still enhance the problem of pipe closure in curved areas because of the reduced flexibility resulting from the overlapping condition of the braided structure.

It is the primary object of the invention to avoid the aforesaid drawbacks. A further object of the invention is to provide a stent structure which allows safe and efficient operation in critical areas such as the end of a food pipe. Still a further object of the invention is a stent which minimizes the risk of pipe closure whatever the configuration of the body passageway. And it is also an object of the invention to provide for methods for manufacturing such a stent which are simple, efficient and economical.

SUMMARY OF THE INVENTION

Accordingly, the flexible self-expandable braided tubular wall forming the stent may comprise a first proximal segment having proximal and distal ends and a first outer diameter, a second distal segment having proximal and distal ends and a second outer diameter smaller than the said first outer diameter, and a third intermediate segment having a proximal end connected to the distal end of the first segment and a distal end connected to the proximal end of the second segment. With such a configuration the stent has a differential geometry which allows a very strong anchor of the first proximal segment in the body passageway due to the higher radial force at that level. The third intermediate segment gives to the braiding a varying steep angle with respect to the longitudinal axis of the tubular wall which raises flexibility and/or radial force depending on the relative size of stent and vessel and on the elasticity of vessel wall; this structure also strongly limits any flattening deformation tendency whereby the deformation of the stent section remains closer to a circle. The second distal segment makes an easier and safer way through curves or at the end of a pipe. The differential geometry thus allows a higher flexibility where needed, i.e., before a curve of the body passageway, and it provides a better bend taking, a smoother way in the curve, and a better force differential to avoid migration under movements of the vessel or when the stent is placed in delicate locations such as the junction of the esophagus with the stomach.

Where the first proximal and second distal segments are cylindrical, the first proximal segment may firmly anchor in the vessel without any risk of damage to the vessel wall or to possible fistulas because of the surface repartition of the pressure of the braiding against the vessel wall, whereas the second distal segment may smoothly bear against the vessel wall, even in strongly narrowed areas.

Where the third intermediate segment is a truncated cone having a base forming the proximal end of the third intermediate segment and a top forming the distal end of the third intermediate segment, the best transitional flexibility and/or radial force repartition is achieved between the first proximal and second distal segments. And when the third intermediate segment is formed of a plurality of consecutive truncated cones connected to one another with each of said truncated cones having a taper oriented towards the distal end of the intermediate segment, with the possibility of having two or more consecutive cones separated by a cylindrical segment connected thereto, stents may be manufactured to meet specific requirements of flexibility, radial force, shaping up and selective anchor in particular conditions of body vessels.

A covering layer of elastic material may surround the tubular wall to prevent ingrowth of unwanted cells through the stent. In a preferred embodiment, a covering layer of elastic material is arranged within the tubular wall to also prevent ingrowth of unwanted cells through the stent; and the stent also enjoys a stronger anchor of its segments in the body cavity due to the direct contact of the braiding therewith. Within this frame, a distal portion of the second distal segment may be uncovered by the covering layer to assure when required a better gripping of the stent to the body cavity in that area, because of the stronger interpenetration between braiding and vessel wall. In a still preferred embodiment, at least a proximal portion of the first proximal segment is not covered by the covering layer to enhance by stronger interpenetration between braiding and vessel wall the essential gripping of the stent in the body passageway in that area of higher radial force. Such an uncovering of the first proximal segment may extend the full length of the first proximal segment to take full advantage of the higher radial force to ensure the safest anchor of that segment in the body passageway. The uncovering of the first proximal segment also prevents food trapping at the ingress of the stent between the first proximal segment and the vessel wall; it also allows a better fluid ingress through the stent if the first proximal segment is somewhat bent in the vessel and does not completely apply there against. And to provide a further safety anchor of the stent in the body passageway, the proximal end of the first proximal segment and/or the distal end of the second distal segment may be flared up.

According to a first method for manufacturing the stent, it is provided to form an elongated mandrel having a first proximal segment having proximal and distal ends and a first outer diameter, a second distal segment having proximal and distal ends and a second outer diameter smaller than said first outer diameter, and a third intermediate segment having a proximal end connected to the distal end of the first proximal segment and a distal end connected to the proximal end of the second segment, to form an elongated tubular braid of spring steel having proximal and distal ends and an inner diameter greater than said first outer diameter of the first segment of the mandrel, to engage said tubular braid over the mandrel, to heat the tubular braid over the mandrel, and to pull during the heating the proximal and distal ends of the tubular braid away from one another on the mandrel to closely radially contract the tubular braid over the segments of the mandrel. As the spring steel of the tubular braid needs anyhow a heat treatment to properly perform the resiliency of the braid, this method takes advantage of this compulsory treatment and of the deformation capacity of the braid to form the differential geometry of the stent in a simple, economical and efficient manner.

According to a second method for manufacturing the stent, it is provided to form an elongated tubular mandrel having a first proximal hollow segment having proximal and distal ends and a first inner diameter, a second distal hollow segment having proximal and distal ends and a second inner diameter smaller than said first inner diameter, and a third intermediate hollow segment having a proximal end connected to the distal end of the first hollow segment and a distal end connected to the proximal end of the second hollow segment, to form an elongated tubular braid of spring steel having proximal and distal ends and an outer diameter greater than the first inner diameter of the first hollow segment of the tubular mandrel, to pull the proximal and distal ends of the elongated tubular braid away from one another to radially contract the tubular braid, to engage the contracted tubular braid into the tubular mandrel, to release the pull on the ends of the tubular braid to radially expand it in the mandrel, and to heat the tubular braid in the mandrel to closely radially expand the tubular braid against the segments of the tubular mandrel. As for the first method, this method basically takes advantage of the need of a heat treatment for the braid to properly perform its resiliency to form the differential geometry of the stent; and in addition the method takes advantage of the self expansion capacity of the braid to form the stent in a simple, economical and efficient manner.

In sum, the present invention relates to a stent for use in a body passageway. A flexible self-expandable braided tubular wall has a first proximal segment having proximal and distal ends and a first outer diameter, a second distal segment having proximal and distal ends and a second outer diameter smaller than said first outer diameter, and a third intermediate segment having a proximal end connected to the distal end of the first segment and a distal end connected to the proximal end of the second segment. The first proximal and second distal segments may be cylindrical. The third intermediate segment may be a truncated cone having a base forming the proximal end of the third intermediate segment and a top forming the distal end of the third intermediate segment. The third intermediate segment may be formed of a plurality of consecutive truncated cones connected to one another, each of said truncated cones having a taper oriented towards the distal end of the intermediate segment. At least two of said consecutive cones may be separated by a cylindrical segment connected thereto. The stent may also have a covering layer of elastic material surrounding the tubular wall, which may be arranged within said tubular wall. At least a proximal portion of the first proximal segment may not be covered by the covering layer. A distal portion of the second distal segment may not be covered by the covering layer. The proximal end of the first proximal segment and/or the distal end of the second distal segment may be flared up.

The present invention also relates to a method for manufacturing a stent, including the steps of: (1) forming an elongated mandrel having a first proximal segment having proximal and distal ends and a first outer diameter, a second distal segment having proximal and distal ends and a second outer diameter smaller than the first outer diameter, and a third intermediate segment having a proximal end connected to the distal end of the first segment and a distal end connected to the proximal end of the second segment; (2) forming an elongated tubular braid of spring steel having proximal and distal ends and an inner diameter greater than the first outer diameter of the first segment of the mandrel; (3) engaging the tubular braid over the mandrel; (4) heating the tubular braid over the mandrel; and, (5) pulling during said heating the proximal and distal ends of the tubular braid away from one another on the mandrel to closely radially contract the tubular braid over the segments of the mandrel.

The present invention also relates to a method for manufacturing the stent, including the steps of: (1) forming an elongated tubular mandrel having a first proximal hollow segment having proximal and distal ends and a first inner diameter, a second distal hollow segment having proximal and distal ends and a second-inner diameter smaller than the first inner diameter, and a third intermediate hollow segment having a proximal end connected to the distal end of the first hollow segment and a distal end connected to the proximal end of the second hollow segment; (2) forming an elongated tubular braid of spring steel having proximal and distal ends and an outer diameter greater than the first inner diameter of the first hollow segment of the tubular mandrel; (3) pulling the proximal and distal ends of the elongated tubular braid away from one another to radially contract the tubular braid; (4) engaging the contracted tubular braid into the tubular mandrel; (5) releasing the pull on the ends of the tubular braid to radially expand it in the mandrel; and, (6) heating the tubular braid in the mandrel to closely radially expand the tubular braid against the segments of the tubular mandrel.

BRIEF DESCRIPTION OF THE DRAWINGS

These and other objects, features and advantages of the invention will become readily apparent from the following detailed description with reference to the accompanying drawings which show, diagrammatically and by way of example only, preferred but still illustrative embodiments of the invention.

FIGS. 4A to 4E illustrate a further method for manufacturing the stent according to the invention.

DESCRIPTION OF PREFERRED EMBODIMENTS

Figure 1:
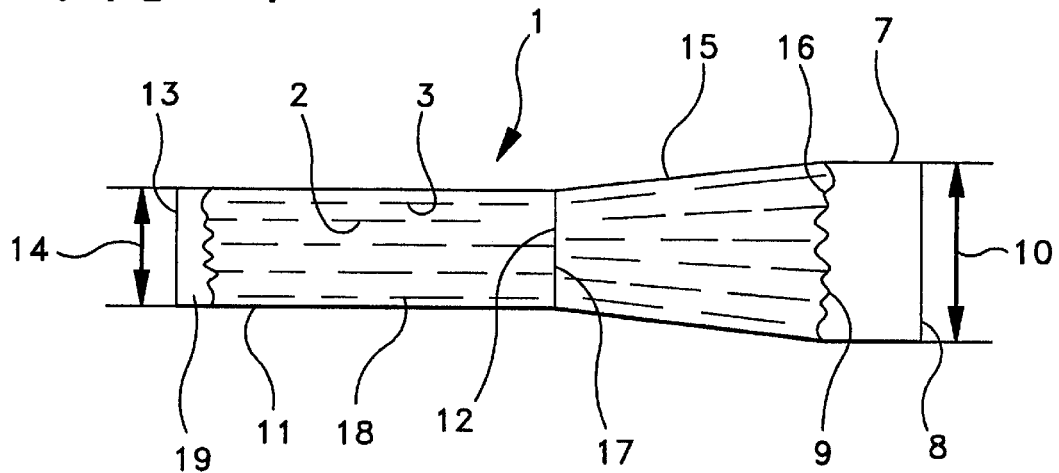
FIG. 1 is a longitudinal view of a first embodiment of the stent.
Figure 2:
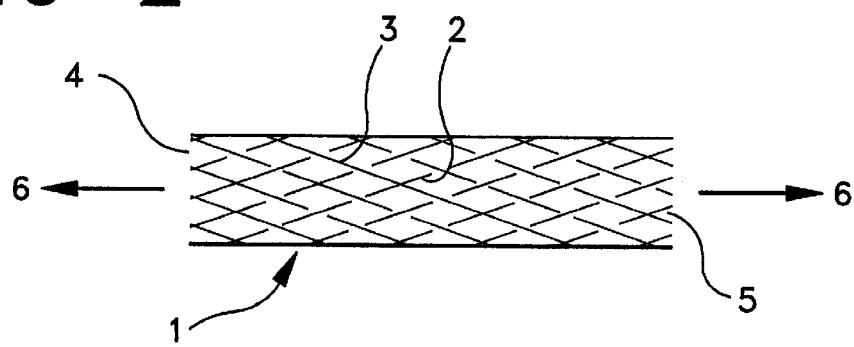
FIG. 2 is an enlarged detail of the stent of FIG. 1.

The stent depicted in FIG. 1 comprises a flexible self-expandable braided tubular wall 1. As shown in FIG. 2 the tubular wall 1 is composed of a first plurality of parallel spring stainless steel wires 2 helically wound in a first direction crossing a second plurality of parallel spring stainless steel wires 3 helically wound in a second direction opposite to the first one. The braided structure assures contraction of the stent in the radial direction when the two ends 4 and 5 of the stent are pulled away from one another as exemplified by arrows 6, and self-expansion of the stent in the radial direction when the pull according to arrows 6 is released. This configuration is well known in the art and needs no further description. Of course, other known braidings or patterns providing the same effect may be used.

The tubular wall 1 of the stent comprises a proximal segment 7 having proximal and distal ends 8 and 9 and an outer diameter 10. The tubular wall 1 further comprises a distal segment 11 having proximal and distal ends 12 and 13 and an outer diameter 14 which is smaller than the outer diameter 10 of the proximal segment 7. Segments 7 and 11 are shown cylindrical but other shapes are possible.

Between segments 7 and 11 is formed an intermediate segment 15 having a proximal end 16 connected to the distal end 9 of proximal segment 7 and a distal end 17 connected to the proximal end 12 of distal segment 11. As shown in FIG. 1, the intermediate segment 15 forms a truncated cone of which the base is forming the proximal end 16 of the intermediate segment and of which the top is forming the distal end 17 of the intermediate segment. Other shapes are available to form the intermediate segment 15.

Within the tubular wall 1 is arranged a covering layer 18 of elastic biocompatible material. In the example shown, this covering layer extends over a portion of the distal segment 11, leaving a distal portion 19 thereof uncovered. The covering layer 18 extends the full length of intermediate segment 15, ending at the junction of intermediate segment 15 with proximal segment 7, i.e., at the distal end 9 of proximal segment 7 (or at proximal end 16 of intermediate segment 15). This layer configuration is not compulsory, and the covering layer 18 may fully cover the distal segment 11 as well as it may partly or fully cover the proximal segment 7. It is also possible to use the stent as described without covering layer 18. The covering layer may also surround the tubular wall 1, partly or fully as described hereabove in connection with the inner layer 18. This covering layer may be applied and affixed to the stent in any manner conventional in the art, for instance by dipping.

Figure 3A:
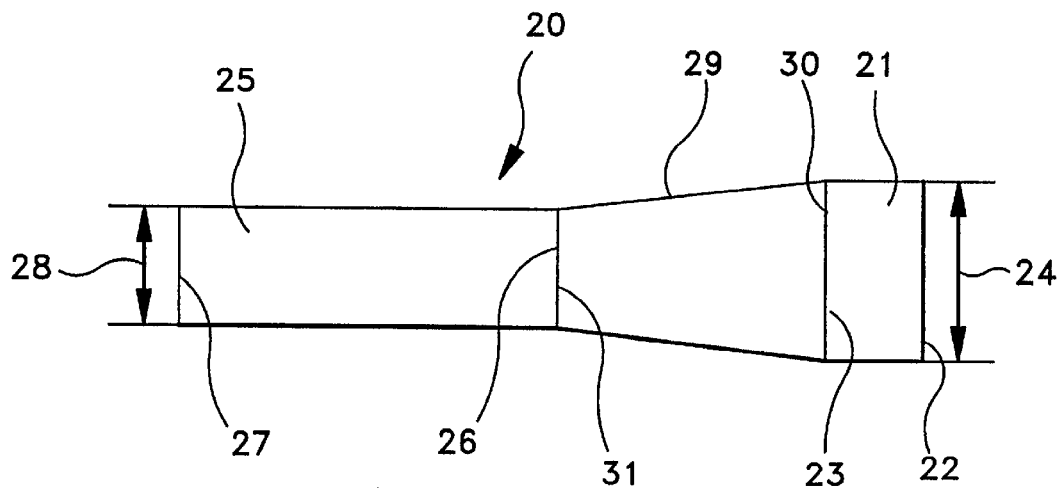
FIGS. 3A to 3C illustrate a first method for manufacturing the stent according to the invention.
Figure 3B:
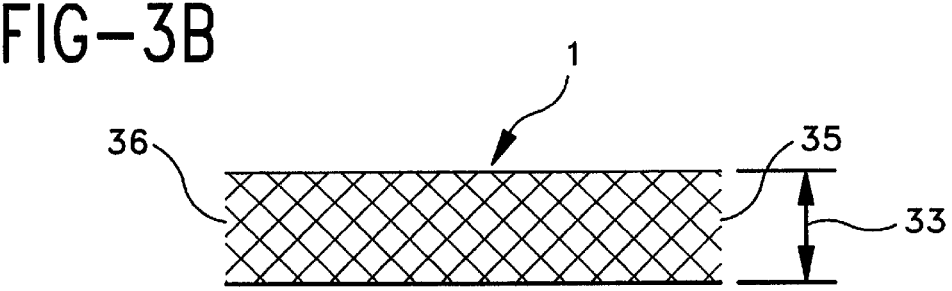
Figure 3C:
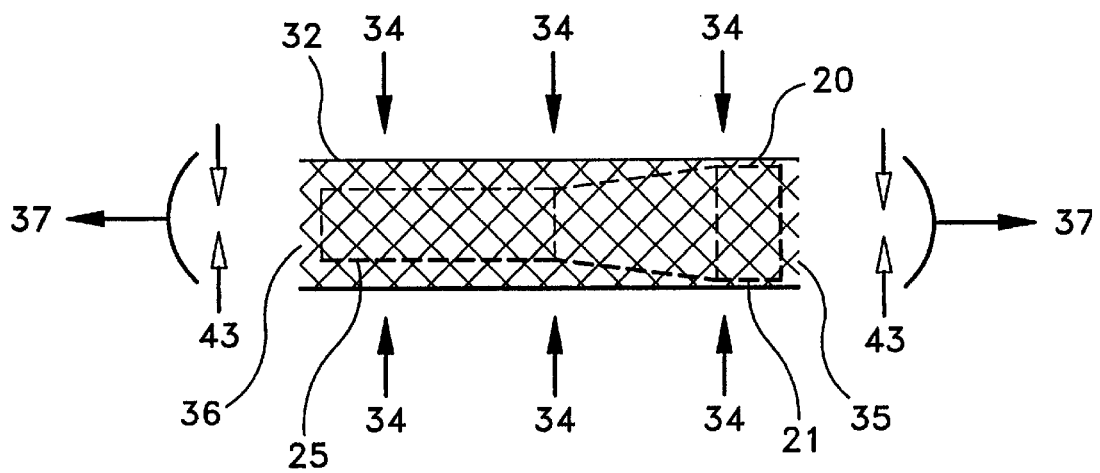
Figure 4A:
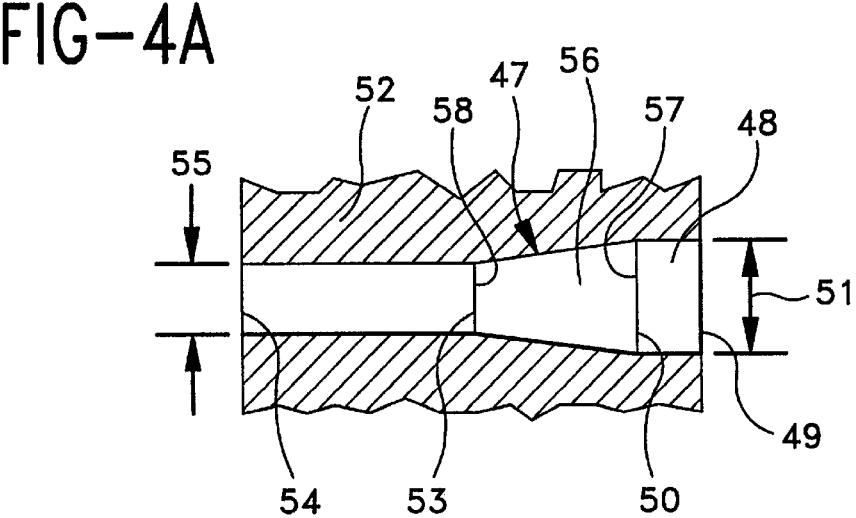
Figure 4E:
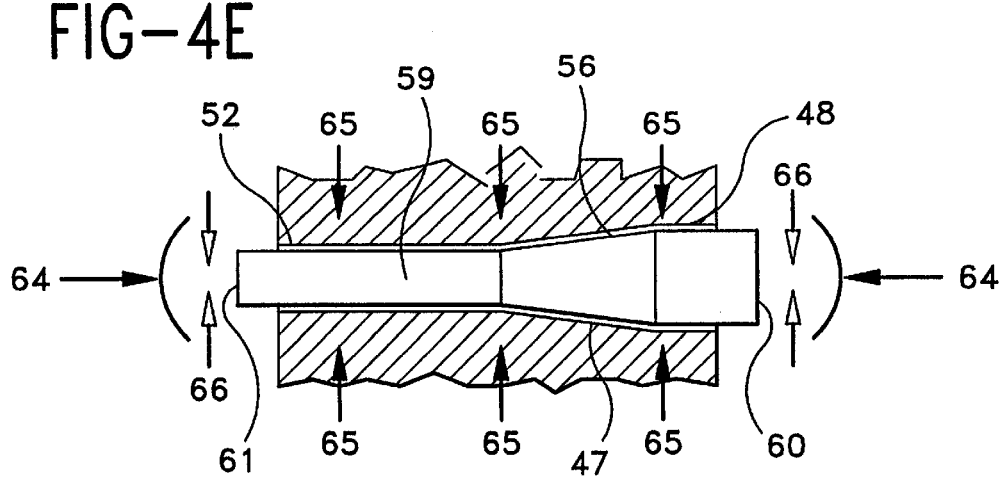

FIGS. 3A to 3C illustrate a method for manufacturing the stent.

As shown in FIG. 3A, an elongated mandrel 20 is formed having a proximal segment 21 having proximal and distal ends 22 and 23 and an outer diameter 24, a distal segment 25 having proximal and distal ends 26 and 27 and an outer diameter 28 smaller than the outer diameter 24 of proximal segment 21, and an intermediate segment 29 having a proximal end 30 connected to the distal end 23 of the proximal segment 21 and a distal end 31 connected to the proximal end 26 of distal segment 25. The intermediate segment 29 also forms a truncated cone of which the base is forming the proximal end 30 of the intermediate segment 29 and of which the top is forming the distal end 31 of the intermediate segment.

As shown in FIG. 3B, an elongated tubular braid 32 is formed of spring stainless steel wire which has proximal and distal ends 35 and 36 and an inner diameter 33 greater than the outer diameter 24 of the proximal segment 21 of mandrel 20.

As shown in FIG. 3C, the tubular braid 32 is engaged over the mandrel 20, it is heated over the mandrel as depicted by arrows 34, and its proximal and distal ends 35 and 36 are pulled away from one another as depicted by arrows 37 to contract it radially on the mandrel as depicted by arrow 43. By this combined heat and pull action, the tubular braid 32 will radially contract upon mandrel 20 and its segments 21, 25 and 29, thereby taking their outer shape which corresponds to the shape of the stent shown in FIG. 1. By the heat treatment, the stent thus obtained will retain the shape of the mandrel and, after contraction thereof by pulling its ends 35 and 36 away from one another or otherwise, it will radially self-expand along the acquired shapes of the mandrel upon release of the contracted status.

FIGS. 4A to 4E show another method for manufacturing the stent according to the invention.

An elongated tubular mandrel 47 is formed having a proximal hollow segment 48 having proximal and distal ends 49 and 50 and an inner diameter 51, a distal hollow segment 52 having proximal and distal ends 53 and 54 and an inner diameter 55 smaller than the inner diameter 51 of the proximal segment 48, and an intermediate hollow segment 56 having a proximal end 57 connected to the distal end 50 of the proximal segment 48 and a distal end 58 connected to the proximal end 53 of the distal segment 52. This intermediate segment also forms a truncated cone as in the previous embodiments, however hollow.

As shown in FIG. 4B, an elongated tubular braid 59 is formed of stainless steel spring wire which has proximal and distal ends 60 and 61 and an outer diameter 62 greater than the inner diameter 51 of the first proximal hollow segment 48 of hollow mandrel 47.

As shown in FIG. 4C, pulling the ends 60 and 61 of the braid 59 away from one another as depicted by arrows 63 radially contracts the tubular braid 59 which is then engaged into the tubular mandrel 47 as shown in FIG. 5D. The pull on the ends 60 and 61 is then released (FIG. 4E) as shown by arrows 64 to expand (arrows 66) the braid radially into the mandrel. Heat is then applied (arrows 65) to the tubular braid in the mandrel. The braid 59 will closely expand within and against the segments 48, 52 and 56 of the hollow mandrel 47, thereby taking their inner shape which corresponds to the shape of the stent shown in FIG. 1. By the heat treatment, the stent will retain the shape of the mandrel and, after radial contraction thereof by pulling the ends away from one another or otherwise, it will radially expand along that acquired shape upon release of the contracted status.

Variants are available without departing from the scope of the invention.

Figure 5:
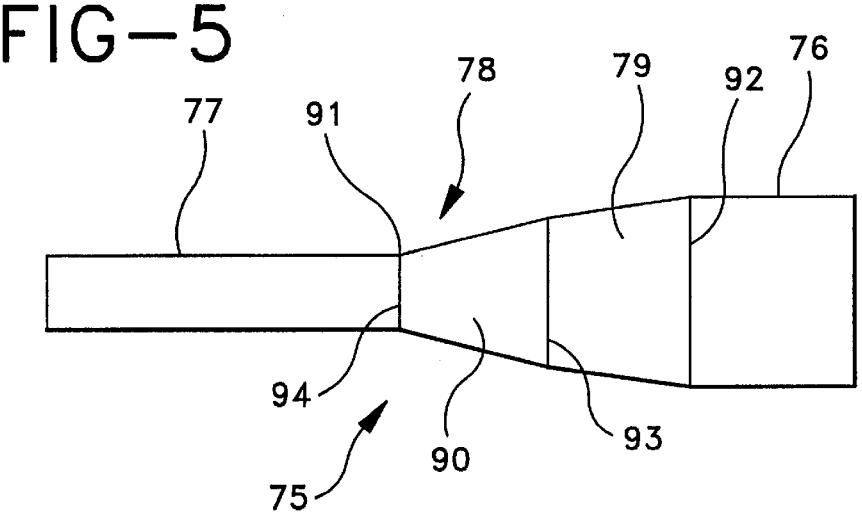
FIG. 5 is a longitudinal view of a second embodiment of the stent.

For instance, the stent as shown in FIG. 5, which also comprises a flexible self-expandable braided tubular wall 75, includes proximal and distal segments 76 and 77 which are cylindrical as for the embodiment of FIG. 1, with the outer diameter of distal segment 77 being smaller than that of the proximal segment 76. The intermediate segment 78 is formed here by two consecutive truncated cover 79 and 90, each of which has a taper oriented towards the distal end 91 of the intermediate segment 78. The truncated cone 79 has a base 92 forming the proximal end of the intermediate segment 78 and a top 93 forming the base of truncated cone 90 the top 94 of which forms the distal end of the intermediate segment 78.

Figure 6:
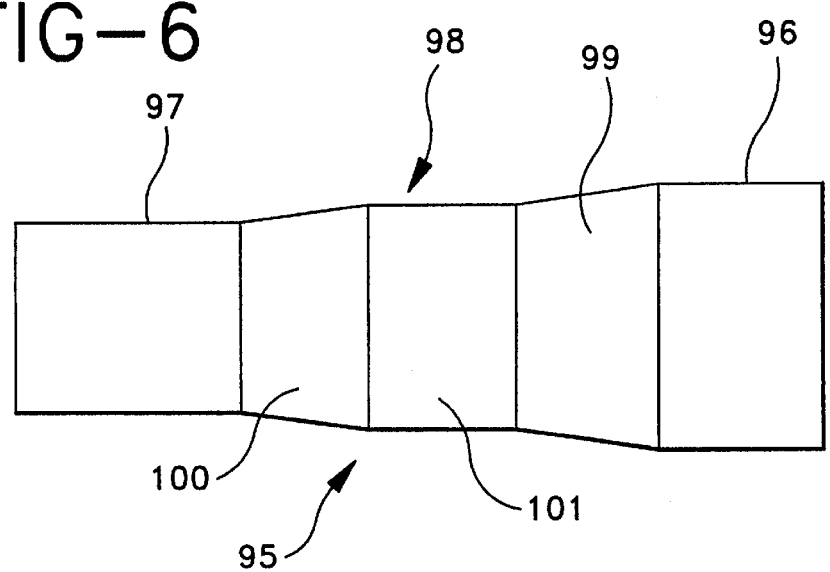
FIG. 6 is a longitudinal view of a third embodiment of the stent.

The stent shown in FIG. 6, also comprises a flexible self-expandable braided tubular wall 95 including proximal and distal segments 96 and 97 which are cylindrical as for the embodiment of FIG. 1, with the outer diameter of distal segment 97 being smaller than that of proximal segment 96. The intermediate segment 98 is here formed by two truncated cones 99 and 100 separated by a cylindrical segment 101. The base of truncated cone 99 forms the proximal end of the intermediate segment 98 and its top forms the base of cylindrical segment 101 the distal end of which forms the base of truncated cone 100 the top of which forms the distal end of the intermediate segment 98.

Figure 7:
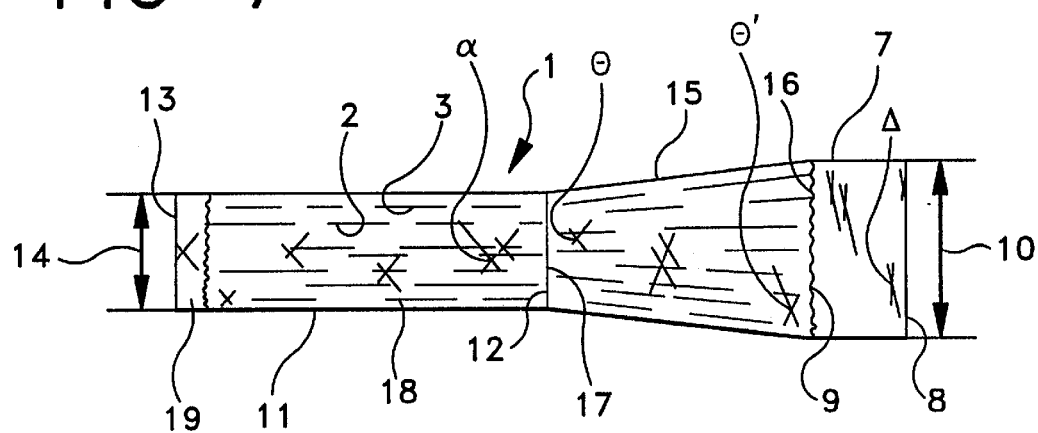
FIG. 7 is a longitudinal view of an embodiment of the invention.

As for the stent of FIG. 1, the stents of FIGS. 5 and 6 may be provided with an inner covering layer of elastic material, and all the variants relating to segments shape and positions of covering layer as previously described and also applicable to the FIGS. 7 and 8 variants. Similarly, these variants may be obtained by the same methods as described hereinbefore.

As a further variant for all the embodiments shown, the proximal end of the proximal segment and/or the distal end of the distal segment may be flared up.

In a still further variant applicable to all the embodiments shown, the stent may be equipped with a covering layer surrounding the tubular wall of the stent. Such a covering layer may be applied and affixed to the stent for instance as described in the document EP-0621015-A1 of the same applicant as that of the present invention which is incorporated hereto by reference.

What is claimed is:

1. A body insertable prosthesis, including:
 a tubular wall disposed about a longitudinal axis and including a first tubular segment having a first segment diameter;
 wherein the tubular wall further includes a second tubular segment disposed distally of the first tubular segment, and the second tubular segment has a proximal end diameter substantially equal to the first segment diameter and is narrowed in the distal direction to a distal end diameter less than the proximal end diameter; and
 wherein the first tubular segment is adapted to exert a first level of radial force therealong when the tubular wall is disposed within a body passageway, thereby to anchor the tubular wall within the body passageway.

2. The prosthesis of claim 1 wherein:
 the tubular wall is radially contractible and radially expandable.

3. The prosthesis of claim 2 wherein:
 the tubular wall is radially contractible responsive to application of an external force, and radially self-expands upon removal of the external force.

4. The prosthesis of claim 1 further including:
 a third tubular segment disposed distally of the second tubular segment and having a third segment diameter substantially equal to said distal end diameter.

5. The prosthesis of claim 4 wherein:
 the third tubular segment is adapted to exert a second level of radial force therealong less than the first level of radial force, and wherein the second tubular segment is adapted to exert radial force at a level that decreases in the distal direction, to provide a transition in radial force between the first tubular segment and the third tubular segment.

6. The prosthesis of claim 1 wherein:
 the second tubular segment comprises a truncated conical segment.

7. The prosthesis of claim 1 wherein:
 the second tubular segment comprises a first truncated conical segment and a second truncated conical segment.

8. The process of claim 7 wherein:
 the tubular wall further includes a cylindrical segment disposed between the first truncated conical segment and the second truncated conical segment.

9. The prosthesis of claim 1 wherein:

the tubular wall is a unitary structure formed of at least one strand of a resilient material.

10. The prosthesis of claim 9 wherein:

the at least one strand of a resilient material comprises at least a first strand wound helically in a first direction, and a second strand wound helically in a second direction different from the first direction.

11. The prosthesis of claim 10 wherein:

the first and second strands are wound in opposite directions and interbraided with one another.

12. The prosthesis of claim 11 wherein:

the first and second strands form a steep angle with respect to the longitudinal axis, and the steep angle varies along the second tubular segment.

13. The prosthesis of claim 12 wherein:

the steep angle increases in the proximal direction along said second tubular segment.

14. The prosthesis of claim 9 wherein:

the tubular wall is radially contractible through application of a force to pull opposite ends thereof away from one another.

15. The prosthesis of claim 14 wherein:

the tubular wall further is adapted to radially self-expand from a radially contracted state in response to a release of said force.

16. The prosthesis of claim 1 further including:

a covering layer extended along at least the second tubular segment.

17. The prosthesis of claim 16 wherein:

the covering layer is elastic.

18. The prosthesis of claim 16 wherein:

the covering layer surrounds the tubular wall.

19. The prosthesis of claim 16 wherein:

the covering layer is extended proximally of the second tubular segment to cover at least a portion of the first tubular segment.

20. The prosthesis of claim 19 wherein:

at least a proximal portion of the first tubular segment remains free of said covering layer.

21. The prosthesis of claim 16 wherein:

the tubular wall further includes a third tubular segment disposed distally of the second tubular segment; and the covering layer extends distally of the second tubular segment along at least a portion of the third tubular segment.

22. A process for forming a truncated conical segment in a radially expandable prosthesis, including:

providing a mandrel with an opening formed therein to define an inside surface, with a segment of the inside surface having a truncated conical shape;

providing a radially expandable tubular structure;

inserting the tubular structure into the opening to a predetermined position with a portion of the tubular structure surrounded by said segment of the inside surface; and while maintaining the tubular structure in the predetermined position, radially expanding the tubular structure into a surface engagement with the inside surface, to form along said portion of the tubular structure a truncated conical shape substantially conforming to said segment of the inside surface.

23. The process of claim 22 further including:

with said portion of the tubular structure in the surface engagement with the inside surface, heating the tubular structure to cause said portion of the tubular structure to retain the truncated conical shape.

24. The process of claim 22 wherein:

the tubular structure has a proximal end and a distal end, and said radially expanding the tubular structure comprises moving the proximal and distal ends toward one another.

25. The process of claim 24 further including:

applying an axial force to pull the proximal and distal ends away from one another against an elastic restoring force to radially contract the tubular structure, wherein said inserting the tubular structure into the opening comprises maintaining the tubular structure in a radially contracted state against the restoring force; and wherein said radially expanding the tubular structure comprises releasing the proximal and distal ends to allow the tubular structure to radially self-expand under the elastic restoring force.

26. A body insertable prosthesis, including:

a radially expandable tubular wall disposed about a longitudinal axis, and incorporating at least one truncated conical segment having a distal end with a distal end diameter and a proximal end with a proximal end diameter larger than the distal end diameter; and a covering layer extended along the truncated conical segment.

27. The prosthesis of claim 26 wherein:

the covering layer is elastic, and surrounds the tubular wall.

28. The prosthesis of claim 26 wherein:

the elastic covering layer is disposed within the tubular wall.

29. The prosthesis of claim 26 wherein:

the tubular wall further includes a proximal segment disposed proximally of the truncated conical segment, and the elastic covering extends proximally of the truncated conical segment along at least a portion of the proximal segment.

30. The prosthesis of claim 26 wherein:

the tubular wall is radially self-expandable, and a radial force of the tubular wall increases in the proximal direction along the at least one truncated conical segment.

31. The prosthesis of claim 26 wherein:

the tubular wall further includes a proximal segment disposed proximally of the truncated conical segment, and having a proximal segment diameter substantially equal to the proximal end diameter.

32. The prosthesis of claim 31 wherein:

the tubular wall further includes a distal segment disposed distally of the truncated conical segment, and having a distal segment diameter substantially equal to the distal end diameter.

33. The prosthesis of claim 26 wherein:

the tubular wall is formed of a plurality of resilient strands.

34. The prosthesis of claim 33 wherein:

the strands are helically wound in first and second different directions.

* * * * *